US009840468B1

(12) United States Patent
Chambournier et al.

(10) Patent No.: US 9,840,468 B1
(45) Date of Patent: Dec. 12, 2017

(54) METHODS FOR THE PREPARATION OF 6-AMINOISOQUINOLINE

(71) Applicant: Aerie Pharmaceuticals, Inc., Durham, NC (US)

(72) Inventors: Gilles Chambournier, Ann Arbor, MI (US); Mitchell A. deLong, Chapel Hill, NC (US)

(73) Assignee: Aerie Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 15/395,068

(22) Filed: Dec. 30, 2016

(51) Int. Cl.
*C07D 217/02* (2006.01)
*C07D 217/22* (2006.01)

(52) U.S. Cl.
CPC ......... *C07D 217/02* (2013.01); *C07D 217/22* (2013.01)

(58) Field of Classification Search
None
See application file for complete search history.

(56) References Cited

FOREIGN PATENT DOCUMENTS

| WO | 2003068749 A1 | 8/2003 |
|----|---------------|--------|
| WO | 2003080578 A1 | 10/2003 |
| WO | 2010019903 A1 | 2/2010 |
| WO | 2010146881 A1 | 12/2010 |
| WO | WO 2016/123627 A1 * | 8/2016 |

OTHER PUBLICATIONS

Fox et al, Journal of Fluorine Chemistry (2013), 155, pp. 62-71.*
Basu MK et al. "Ultrasound-promoted highly efficient reduction of aromatic nitro compounds to the aromatic amines by samarium/ammonium chloride." Tetrahedron Lett 41:5603-5606, 2000.
Poradowska H et al. "The Preparation of 6-Aminoisoquinoline." Synthesis 11:733, 1975.
Sharma U et al. "Highly Chemo- and Regioselective Reduction of Aromatic Nitro Compounds Catalyzed by Recyclable Copper(II) as well as Cobalt(II) Phthalocyanines." Advanced Synthesis and Catalysis 352:1834-1840, 2010.
Guha NR et al. "Solid supported rhodium(0) nanoparticles: an efficient catalyst for chemo- and regio-selective transfer hydrogenation of nitroarenes to anilines under microwave irradiation." Tetradedron Lett 55:2912-2916, 2014.
Kumar M et al. "Catalyst-free water mediated reduction of nitroarenes using glucose as a hydrogen source." RSC Advances 3:4894-4898, 2013.
Sharma U et al. "Catalyst-free water mediated reduction of nitroarenes using glucose as a hydrogen source." Green Chem. 14:2289-2293, 2012.
Sharma U et al. "Phosphene-Free Green Protocol for Selective Nitro Reduction with an Iron-Based Catalyst." Chemistry—A European Journal 17:5903-5907, 2011.
Sturdivant JM et al. "Identification of intermediates in the stepwise reduction of 1,3-dichloro-6-nitroisoquinoline to 6-aminoisoquinoline." 248th National Meeting of the American Chemical Society, Aug. 2014, MEDI 153.

* cited by examiner

*Primary Examiner* — Zinna Northington-Davis
(74) *Attorney, Agent, or Firm* — K&L Gates LLP; Louis C. Cullman; Benjamin D. Heuberger

(57) ABSTRACT

Described are methods for the preparation of 6-aminoisoquinoline, a useful intermediate compound in the synthesis of kinase inhibitors.

27 Claims, No Drawings

METHODS FOR THE PREPARATION OF 6-AMINOISOQUINOLINE

TECHNICAL FIELD

The present disclosure relates to methods for preparing 6-aminoisoquinoline, an intermediate compound in the synthesis of compounds useful for treating kinase-related diseases and/or disorders.

BACKGROUND

Several kinase inhibitors useful for treating a variety of diseases and/or disorders possess a 6-aminoisoquinoline moiety. There exists a need for a process to produce 6-aminoisoquinoline in an efficient, scaleable, and reproducible manner that will allow for the generation of large scale quantities.

SUMMARY OF THE INVENTION

In one aspect, disclosed is a method of preparing 6-aminoisoquinoline,

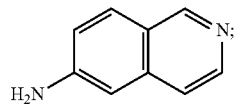

the method may comprise converting 1,3-dichloro-6-nitroisoquinoline,

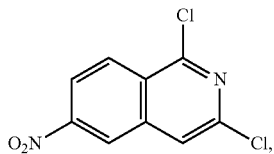

to 6-aminoisoquinoline, then purifying the material to at least about 99.9% pure using a triple purification system.

DETAILED DESCRIPTION

Disclosed herein are methods for the preparation of 6-aminoisoquinoline. 6-Aminoisoquinoline is a useful intermediate for the synthesis of kinase inhibitors. 6-Aminoisoquinoline may be prepared in a manner that efficiently generates large scale quantities and enables the production of kinase inhibitors, which can be used to treat or prevent kinase-related diseases and/or disorders. These include diseases and disorders related to the eye (e.g., glaucoma and ocular hypertension, and retinal diseases such as AMD, Diabetic Retinopathy, DME and inflammatory diseases of the retina), the respiratory system, the skin, and the cardiovascular system, and for diseases characterized by abnormal growth, such as cancers.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" or "at least" used in connection with a quantity is inclusive of the stated value and has the meaning dictated by the context (for example, it includes at least the degree of error associated with the measurement of the particular quantity). The modifier "about" or "at least" should also be considered as disclosing the range defined by the absolute values of the two endpoints. For example, the expression "from about or least 2 to about or at least 4" also discloses the range "from 2 to 4." The term "about or at least" may refer to plus or minus 10% of the indicated number. For example, "about 10%" may indicate a range of 9% to 11%, and "about 1" may mean from 0.9-1.1. Other meanings of "about or at least" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl" as used herein, means a straight or branched, saturated hydrocarbon chain containing from 1 to 10 carbon atoms. The term "lower alkyl" or "$C_1$-$C_6$ alkyl" means a straight or branched chain hydrocarbon containing from 1 to 6 carbon atoms. The term "$C_3$-$C_7$ branched alkyl" means a branched chain hydrocarbon containing from 3 to 7 carbon atoms. The term "$C_1$-$C_4$ alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. An alkyl may be substituted or unsubstituted.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—. An alkylene may be substituted or unsubstituted.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl. Aryl groups may be substituted or unsubstituted. Suitable substituents of the aryl groups may be, but are not limited to alkyl, nitro, cyano, halo, haloalkyl and sulfonyl.

The term "halogen" or "halo" as used herein, means Cl, Br, I, or F.

The term "haloalkyl" as used herein, means at least one halo group, as defined herein, appended to the parent molecular moiety through an alkyl group, as defined herein. Representative examples of haloalkyl include trifluoromethyl and 2,2,2-trifluoroethyl.

The term "catalyst loading" as used herein, refers to the amount of catalyst used in a reaction, and is typically reported as mol %. The catalyst loading is determined as a molar percentage of the limiting reactant of a particular reaction. For example, a reaction with 1 mole of starting material may require 0.1 moles of catalyst, which is equivalent to 10.0 mol % catalyst loading.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc., at normal temperatures and pressures.

For the recitation of numeric ranges herein, each intervening number there between with the same degree of precision is explicitly contemplated. As examples, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Methods of Preparing 6-Aminoisoquinoline

In one aspect, disclosed are methods for the preparation of 6-aminoisoquinoline:

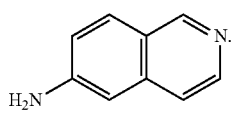 [SMILES: Nc1ccc2cnccc2c1]

The methods may include reacting the compound of formula (I), wherein X is halogen or OSO$_2$R$^a$; and R$^a$ is aryl, alkyl or haloalkyl; with the compound of formula (II), wherein R is alkyl, to form the compound of formula (III), wherein R is alkyl; transforming the compound of formula (III) to 2-(carboxymethyl)-4-nitrobenzoic acid (compound 1) by hydrolysis of the esters and decarboxylation; reacting 2-(carboxymethyl)-4-nitrobenzoic acid (compound 1) with urea to form the bicyclic 6-nitroisoquinoline-1,3(2H, 4H)-dione (compound 2); converting 6-nitroisoquinoline-1,3 (2H,4H)-dione (compound 2) to 1,3-dichloro-6-nitroisoquinoline (compound 3) by reaction with R$^1$—P(O)Cl$_2$, wherein R$^1$ is alkyl, aryl, or chloro; and converting 1,3-dichloro-6-nitroisoquinoline (compound 3) to 6-aminoisoquinoline (compound 4).

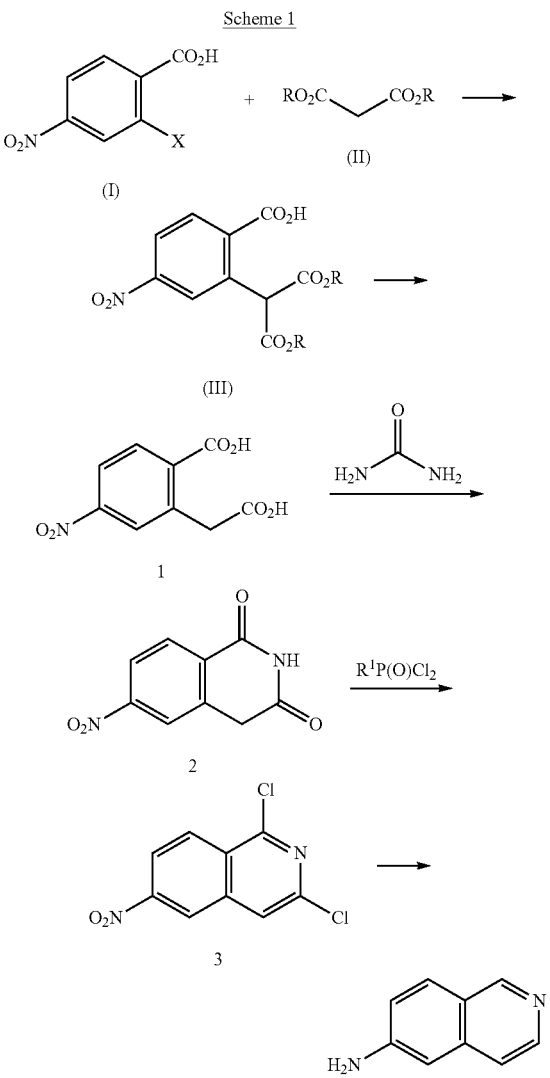

The methods may comprise converting 1,3-dichloro-6-nitroisoquinoline (compound 3),

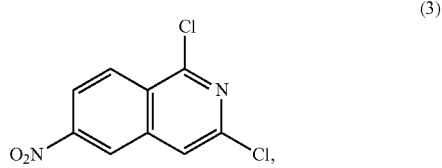 [SMILES: O=[N+]([O-])c1ccc2c(Cl)nc(Cl)cc2c1]

to 6-aminoisoquinoline (compound 4).

In certain embodiments, converting 1,3-dichloro-6-nitroisoquinoline (compound 3) to 6-aminoisoquinoline (compound 4) comprises hydrogenation of 1,3-dichloro-6-nitroisoquinoline (compound 3) in the presence of a metal catalyst. In certain embodiments, the metal catalyst comprises a transition metal. In certain embodiments, the transition metal is selected from the group consisting of palladium, platinum, nickel, rhodium, ruthenium, iridium, cobalt and iron, and combinations thereof. In certain embodiments, the metal catalyst is palladium on carbon. The total catalyst loading in the reaction may be about or at least 0.1 mol % to about or at least 5.0 mol %. For example, the catalyst loading may be about or at least about or at least 0.1 mol %, about or at least 0.2 mol %, about or at least 0.3 mol %, about or at least 0.4 mol %, about or at least 0.5 mol %, about or at least 0.6 mol %, about or at least 0.7 mol %, about or at least 0.8 mol %, about or at least 0.9 mol %, about or at least 1.0 mol %, about or at least 1.1 mol %, about or at least 1.2 mol %, about or at least 1.3 mol %, about or at least 1.4 mol %, about or at least 1.5 mol %, about or at least 1.6 mol %, about or at least 1.7 mol %, about or at least 1.8 mol %, about or at least 1.9 mol %, about or at least 2.0 mol %, about or at least 2.1 mol %, about or at least 2.2 mol %, about or at least 2.3 mol %, about or at least 2.4 mol %, about or at least 2.5 mol %, about or at least 2.6 mol %, about or at least 2.7 mol %, about or at least 2.8 mol %, about or at least 2.9 mol %, about or at least 3.0 mol %, about or at least 3.1 mol %, about or at least 3.2 mol %, about or at least 3.3 mol %, about or at least 3.4 mol %, about or at least 3.5 mol %, about or at least 3.6 mol %, about or at least 3.7 mol %, about or at least 3.8 mol %, about or at least 3.9 mol %, about or at least 4.0 mol %, about or at least 4.1 mol %, about or at least 4.2 mol %, about or at least 4.3 mol %, about or at least 4.4 mol %, about or at least 4.5 mol %, about or at least 4.6 mol %, about or at least 4.7 mol %, about or at least 4.8 mol %, about or at least 4.9 mol %, or about or at least 5.0 mol %. The catalyst may be added in portions during the course of the conversion. The catalyst may be added such that the entirety of the catalyst is added at one time.

1,3-dichloro-6-nitroisoquinoline (compound 3) may be converted to 6-aminoisoquinoline (compound 4) in the presence of a solvent or mixture of solvents. Any suitable solvent that is compatible with the components of the reaction mixture may be used. Suitably, a solvent will be selected such that the starting materials will be at least partially soluble (or fully soluble) and will allow the reaction mixture to be heated, if necessary, to a temperature sufficient for the reaction to produce 6-aminoisoquinoline (compound 4). The solvents may include, but are not limited to: ethers such as diethyl ether, dibutyl ether, 1,2-dimethoxyethane, diglyme, t-butyl methyl ether, tetrahydrofuran and dioxane; aliphatic or aromatic hydrocarbon solvents such as benzene, xylene, toluene, hexane, and pentane; polar protic solvents such as methanol, ethanol, n-propanol, isopropanol, n-butanol, acetic acid and water; or any combination of two or more solvents.

In certain embodiments, the solvent is tetrahydrofuran. In certain embodiments, the solvent is a mixture of tetrahydrofuran and methanol.

In certain embodiments, the converting of 1,3-dichloro-6-nitroisoquinoline (compound 3) to 6-aminoisoquinoline (compound 4) may further comprise heating. For example, the reaction mixture may be heated at a temperature greater than ambient or room temperature, wherein ambient or room temperature is about 18° C. to about 25° C. The reaction mixture may be heated at a temperature of about 25° C. to about 60° C., or about 30° C. to about 60° C. The reaction mixture may be heated at a temperature of about or at least 25° C., about or at least 30° C., about or at least 35° C., about or at least 40° C., about or at least 45° C., about or at least 50° C., about or at least 55° C., or about or at least 60° C. The reaction mixture may be heated at a temperature of less than about 60° C., less than about 55° C., less than about 50° C., less than about 45° C., less than about 40° C., less than about 35° C., or less than about 30° C.

In certain embodiments, the converting of 1,3-dichloro-6-nitroisoquinoline (compound 3) to 6-aminoisoquinoline (compound 4) may further comprise pressurizing the reaction under an atmosphere of hydrogen. For example, the reaction mixture may be pressurized to a pressure greater than atmospheric pressure, wherein ambient or atmospheric pressure is about or at least 0.1 MP. The reaction mixture may be pressurized to about 0.1 MP to about 1.0 MP, or about 0.2 MP to about 0.8 MP. The reaction mixture may be pressurized to at least 0.1 MP, at least 0.2 MP, at least 0.3 MP, at least 0.4 MP, at least 0.5 MP, at least 0.6 MP, at least 0.7 MP, or at least 0.8 MP. The reaction mixture may be pressurized to less than 0.8 MP, less than 0.7 MP, less than 0.6 MP, less than 0.5 MP, less than 0.4 MP, less than 0.3 MP, or less than about 0.2 MP. The reaction mixture may be pressurized to about 0.1 MP, about 0.2 MP, about 0.3 MP, about 0.4 MP, about 0.5 MP, about 0.6 MP, about 0.7 MP, or about 0.8 MP.

In certain embodiments, other components may also be added to the reaction mixture, such as an acid, a base or a salt. For example, potassium carbonate may be added to the reaction mixture.

In certain embodiments, the converting of 1,3-dichloro-6-nitroisoquinoline (compound 3) to 6-aminoisoquinoline (compound 4) is achieved by hydrogenation of the nitro group followed by hydrogenation of the carbon-chlorine bonds. For example, complete hydrogenation of the nitro group may be achieved in tetrahydrofuran in the presence of palladium on carbon at a pressure of about or at least 0.6 MP and a temperature of about or at least 45° C. Partial hydrogenation of the carbon-chlorine bonds may occur under these conditions. Complete hydrogenation of the carbon-chlorine bonds may be achieved by adding a second solvent, such as methanol; adding a salt, such as potassium carbonate; and adding palladium on carbon catalyst, and allowing the reaction to proceed at a pressure of about or at least 0.6 MP and a temperature of about or at least 45° C.

The methods may comprise allowing the conversion of 1,3-dichloro-6-nitroisoquinoline (compound 3) to 6-aminoisoquinoline (compound 4) to proceed for a period of time sufficient to form 6-aminoisoquinoline (compound 4). For example, the reaction may be allowed to proceed for about 2 hours to about 4 days. The reaction may be allowed to proceed for about 2 to about 8 hours for hydrogenation of the nitro group to the amino group. The reaction may be allowed to proceed for an additional 2 hours to 4 days for hydrogenation of the carbon-chlorine bonds to be complete.

The methods may form 6-aminoisoquinoline (compound 4) in a yield of about 20% to about 100%, e.g., about 20% to about 99%. The methods may form 6-aminoisoquinoline (compound 4) in about or at least 20%, about or at least 25%, about or at least 30%, about or at least 35%, about or at least 40%, about or at least 45%, about or at least 50%, about or at least 51%, about or at least 52%, about or at least 53%, about or at least 54%, about or at least 55%, about or at least 56%, about or at least 57%, about or at least 58%, about or at least 59%, about or at least 60%, about or at least 61%, about or at least 62%, about or at least 63%, about or at least 64%, about or at least 65%, about or at least 66%, about or at least 67%, about or at least 68%, about or at least 69%, about or at least 70%, about or at least 71%, about or at least 72%, about or at least 73%, about or at least 74%, about or at least 75%, about or at least 76%, about or at least 77%, about or at least 78%, about or at least 79%, about or at least 80%, about or at least 81%, about or at least 82%, about or at least 83%, about or at least 84%, about or at least 85%, about or at least 86%, about or at least 87%, about or at least 88%, about or at least 89%, about or at least 90%, about or at least 91%, about or at least 92%, about or at least 93%, about or at least 94%, about or at least 95%, about or at least 96%, about or at least 97%, about or at least 98%, about or at least 99% or about or at least 100% yield.

The methods may form 6-aminoisoquinoline (compound 4) with a purity of greater than or equal to about 60%, greater than or equal to about 65%, greater than or equal to about 70%, greater than or equal to about 75%, greater than or equal to about 80%, greater than or equal to about 85%, greater than or equal to about 90%, greater than or equal to about 95%, greater than or equal to about 96%, greater than or equal to about 97%, greater than or equal to about 98%, or greater than or equal to about 99%, or greater than or equal to about 99.5%, or greater than or equal to about 99.9% as determined by HPLC.

In certain embodiments, one or more impurities or byproducts may be formed by the methods. For example, the following compounds may form while carrying out the disclosed methods (some of them arising from impurities in the starting materials):

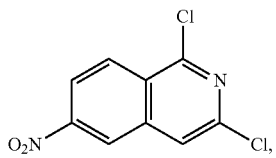 [SMILES: O=[N+]([O-])c1ccc2c(Cl)nc(Cl)cc2c1]

1,3-dichloro-6-nitroisoquinoline;

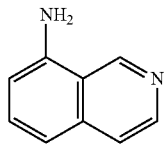 [SMILES: Nc1cccc2ccncc12]

isoquinolin-8-amine;

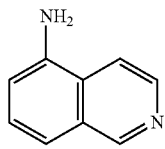 [SMILES: Nc1cccc2cnccc12]

isoquinolin-5-amine;

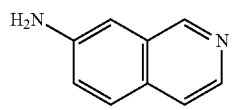

isoquinolin-7-amine;

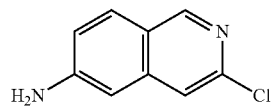 [SMILES: Nc1ccc2cnc(Cl)cc2c1]

3-chloroisoquinolin-6-amine;

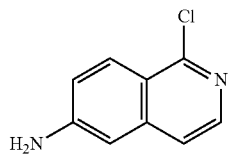 [SMILES: Nc1ccc2c(Cl)nccc2c1]

1-chloroisoquinolin-6-amine; and

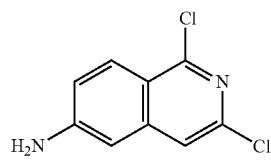 [SMILES: Nc1ccc2c(Cl)nc(Cl)cc2c1]

1,3-dichloroisoquinolin-6-amine;
or any combination thereof.

The methods may further comprise reacting 6-nitroisoquinoline-1,3(2H,4H)-dione (compound 2),

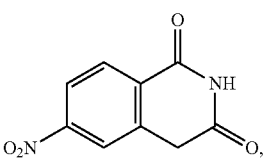

(2)

with $R^1$—P(O)Cl$_2$, wherein $R^1$ is aryl, alkyl or chloro; to form 1,3-dichloro-6-nitroisoquinoline (compound 3).

In certain embodiments, $R^1$ is unsubstituted or substituted aryl. In certain embodiments, $R^1$ is unsubstituted or substituted phenyl. In certain embodiments, $R^1$ is phenyl.

The reaction of 6-nitroisoquinoline-1,3(2H,4H)-dione (compound 2) with $R^1$—P(O)Cl$_2$ may further comprise a solvent or mixture of solvents. Any suitable solvent that is compatible with the components of the reaction mixture may be used. Suitably, a solvent will be selected such that the starting materials will be at least partially soluble (or fully soluble) and will allow the reaction mixture to be heated, if necessary, to a temperature sufficient for the reaction to produce 1,3-dichloro-6-nitroisoquinoline (compound 3). The reacting of 6-nitroisoquinoline-1,3(2H, 4H)-dione (compound 2) with $R^1$—P(O)Cl$_2$ may not comprise a solvent. In certain embodiments, $R^1$—P(O)Cl$_2$ is the solvent.

In certain embodiments, the reacting of 6-nitroisoquinoline-1,3(2H,4H)-dione (compound 2) with $R^1$—P(O)Cl$_2$ may further comprise heating. For example, the reaction mixture may be heated at a temperature greater than ambient or room temperature, wherein ambient or room temperature is about 18° C. to about 25° C. The reaction mixture may be heated at a temperature of about 25° C. to about 160° C., or about 30° C. to about 150° C. The reaction mixture may be heated at a temperature of at least 90° C., at least 100° C., at least 110° C., at least 120° C., at least 130° C., or at least 140° C. The reaction mixture may be heated at a temperature of less than 140° C., less than 130° C., less than 120° C., less than 110° C., or less than 100° C. The reaction mixture may be heated at a temperature of about 90° C., about 100° C., about 110° C., about 120° C., about 130° C., about 140° C., about 150° C., or about 160° C.

In certain embodiments, other components may also be added to the reaction mixture, such as an acid, a base or a salt.

The methods may comprise allowing the reacting of 6-nitroisoquinoline-1,3(2H,4H)-dione (compound 2) with $R^1$—P(O)Cl$_2$ to proceed for a period of time sufficient to form 1,3-dichloro-6-nitroisoquinoline (compound 3). For example, the reaction may be allowed to proceed for about 20 minutes to about 12 hours, or about 1 hour to about 4 hours.

The methods may form 1,3-dichloro-6-nitroisoquinoline (compound 3) in a yield of about or at least 20% to about or at least 100%, e.g., about or at least 20% to about or at least 99%. The method may form 1,3-dichloro-6-nitroisoquinoline (compound 3) in about or at least 20%, about or at least 25%, about or at least 30%, about or at least 35%, about or at least 40%, about or at least 45%, about or at least 50%, about or at least 51%, about or at least 52%, about or at least 53%, about or at least 54%, about or at least 55%, about or at least 56%, about or at least 57%, about or at least 58%, about or at least 59%, about or at least 60%, about or at least 61%, about or at least 62%, about or at least 63%, about or at least 64%, about or at least 65%, about or at least 66%, about or at least 67%, about or at least 68%, about or at least 69%, about or at least 70%, about or at least 71%, about or at least 72%, about or at least 73%, about or at least 74%, about or at least 75%, about or at least 76%, about or at least 77%, about or at least 78%, about or at least 79%, about or at least 80%, about or at least 81%, about or at least 82%, about or at least 83%, about or at least 84%, about or at least 85%, about or at least 86%, about or at least 87%, about or at least 88%, about or at least 89%, about or at least 90%, about or at least 91%, about or at least 92%, about or at least 93%, about or at least 94%, about or at least 95%, about or at least 96%, about or at least 97%, about or at least 98%, about or at least 99% or about or at least 100% yield.

The method may form 1,3-dichloro-6-nitroisoquinoline (compound 3) with a purity of greater than or equal to about 60%, greater than or equal to about 65%, greater than or equal to about 70%, greater than or equal to about 75%, greater than or equal to about 80%, greater than or equal to about 85%, greater than or equal to about 90%, greater than or equal to about 95%, greater than or equal to about 96%, greater than or equal to about 97%, greater than or equal to about 98%, or greater than or equal to about 99%, as determined by HPLC.

The methods may further comprise reacting 2-(carboxymethyl)-4-nitrobenzoic acid (compound 1),

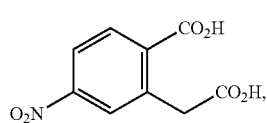

(1)

with urea in the presence of an acid, to form 6-nitroisoquinoline-1,3(2H, 4H)-dione (compound 2).

In certain embodiments, the acid is an organic acid selected from the group consisting of formic acid, acetic acid, propionic acid, and combinations thereof. In certain embodiments the acid is acetic acid.

The reacting of 2-(carboxymethyl)-4-nitrobenzoic acid (compound 1) with urea in the presence of an acid may further comprise a solvent or mixture of solvents. Any suitable solvent that is compatible with the components of the reaction mixture may be used. Suitably, a solvent will be selected such that the starting materials will be at least partially soluble (or fully soluble) and will allow the reaction mixture to be heated, if necessary, to a temperature sufficient for the reaction to produce 1,3-dichloro-6-nitroisoquinoline (compound 2). The reacting of 2-(carboxymethyl)-4-nitrobenzoic acid (compound 1) with urea in the presence of an acid may not comprise an additional solvent. In certain embodiments, the organic acid (e.g., acetic acid) is added in a sufficient amount to be the solvent.

In certain embodiments, the reacting of 2-(carboxymethyl)-4-nitrobenzoic acid (compound 1) with urea in the presence of an acid may further comprise heating. For example, the reaction mixture may be heated at a temperature greater than ambient or room temperature, wherein ambient or room temperature is about 18° C. to about 25° C. The reaction mixture may be heated at a temperature of about 25° C. to about 140° C., or about 90° C. to about 140° C. The reaction mixture may be heated at a temperature of at least 60° C., at least 70° C., at least 80° C., at least 90° C., at least 100° C., or at least 110° C. The reaction mixture may be heated at a temperature of less than 110° C., less than 100° C., less than 90° C., less than 80° C., or less than 70° C. The reaction mixture may be heated at a temperature of about 70° C., about 80° C., about 90° C., about 100° C., about 110° C., about 120° C., about 130° C., or about 140° C.

In certain embodiments, other components may also be added to the reaction mixture, such as an acid, a base or a salt.

The methods may comprise allowing the reacting of 2-(carboxymethyl)-4-nitrobenzoic acid (compound 1) with urea in the presence of an acid to proceed for a period of time sufficient to form 6-nitroisoquinoline-1,3(2H, 4H)-dione (compound 2). For example, the reaction may be allowed to proceed for about 20 minutes to about 12 hours, or about 1 hour to about 8 hours.

The methods may form 6-nitroisoquinoline-1,3(2H,4H)-dione (compound 2) in a yield of about 20% to 100%, e.g., about 20% to about 99%. The methods may form 6-nitroisoquinoline-1,3(2H,4H)-dione (compound 2) in about or at least 20%, about or at least 25%, about or at least 30%, about or at least 35%, about or at least 40%, about or at least 45%, about or at least 50%, about or at least 51%, about or at least 52%, about or at least 53%, about or at least 54%, about or at least 55%, about or at least 56%, about or at least 57%, about or at least 58%, about or at least 59%, about or at least 60%, about or at least 61%, about or at least 62%, about or at least 63%, about or at least 64%, about or at least 65%, about or at least 66%, about or at least 67%, about or at least 68%, about or at least 69%, about or at least 70%, about or at least 71%, about or at least 72%, about or at least 73%, about or at least 74%, about or at least 75%, about or at least 76%, about or at least 77%, about or at least 78%, about or at least 79%, about or at least 80%, about or at least 81%, about or at least 82%, about or at least 83%, about or at least 84%, about or at least 85%, about or at least 86%, about or at least 87%, about or at least 88%, about or at least 89%, about or at least 90%, about or at least 91%, about or at least 92%, about or at least 93%, about or at least 94%, about or at least 95%, about or at least 96%, about or at least 97%, about or at least 98%, about or at least 99% or about or at least 100% yield.

The methods may form 6-nitroisoquinoline-1,3(2H,4H)-dione (compound 2) with a purity of greater than or equal to about 60%, greater than or equal to about 65%, greater than or equal to about 70%, greater than or equal to about 75%, greater than or equal to about 80%, greater than or equal to about 85%, greater than or equal to about 90%, greater than or equal to about 95%, greater than or equal to about 96%, greater than or equal to about 97%, greater than or equal to about 98%, or greater than or equal to about 99%, as determined by HPLC.

The methods may further comprise reacting a compound of formula (III),

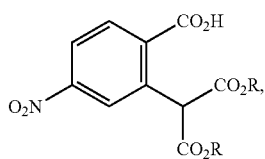

wherein R is alkyl; with a base, to form 2-(carboxymethyl)-4-nitrobenzoic acid (compound 1).

In certain embodiments, R is $C_1$-$C_6$ alkyl. In certain embodiments, R is $C_1$-$C_4$ alkyl. In certain embodiments R is ethyl. In certain embodiments, the compound of formula (III) is 2-(1,3-diethoxy-1,3-dioxopropan-2-yl)-4-nitrobenzoic acid.

In certain embodiments, the base is an alkali metal hydroxide, an alkaline earth metal hydroxide, or a combination thereof. Alkali metal hydroxides include LiOH, NaOH, KOH, RbOH and CsOH. Alkaline earth metal hydroxides include $Be(OH)_2$, $Mg(OH)_2$, $Ca(OH)_2$, $Sr(OH)_2$, and $Ba(OH)_2$. In certain embodiments the base is KOH.

The reacting of a compound of formula (III) with a base may further comprise a solvent or mixture of solvents. Any suitable solvent that is compatible with the components of the reaction mixture may be used. Suitably, a solvent will be selected such that the starting materials will be at least partially soluble (or fully soluble) and will allow the reaction mixture to be heated, if necessary, to a temperature sufficient for the reaction to form 2-(carboxymethyl)-4-nitrobenzoic acid (compound 1). In certain embodiments, the solvent is water.

In certain embodiments, the reacting of a compound of formula (III) with a base may further comprise heating. For example, the reaction mixture may be heated at a temperature greater than ambient or room temperature, wherein ambient or room temperature is about 18° C. to about 25° C. The reaction mixture may be heated at a temperature of about 25° C. to about 100° C. The reaction mixture may be heated at a temperature of at least 60° C., at least 70° C., at least 80° C., at least 90° C., or at least 100° C. The reaction mixture may be heated at a temperature of less than 100° C., less than 90° C., less than 80° C., less than 70° C., or less than 60° C. The reaction mixture may not be heated, but allowed to proceed at ambient or room temperature.

The methods may comprise allowing the reacting of compound of formula (III) with a base to proceed for a period of time sufficient to form 2-(carboxymethyl)-4-nitrobenzoic acid (compound 1). For example, the reaction may be allowed to proceed for about 20 minutes to about 24 hours, about 1 hour to about 18 hours, or about 6 hours to about 16 hours.

The methods may form 2-(carboxymethyl)-4-nitrobenzoic acid (compound 1) in a yield of about 20% to 100%, or about 20% to about 99%. The methods may form 2-(carboxymethyl)-4-nitrobenzoic acid (compound 1) in about or at least 20%, about or at least 25%, about or at least 30%, about or at least 35%, about or at least 40%, about or at least 45%, about or at least 50%, about or at least 51%, about or at least 52%, about or at least 53%, about or at least 54%, about or at least 55%, about or at least 56%, about or at least 57%, about or at least 58%, about or at least 59%, about or at least 60%, about or at least 61%, about or at least 62%, about or at least 63%, about or at least 64%, about or at least 65%, about or at least 66%, about or at least 67%, about or at least 68%, about or at least 69%, about or at least 70%, about or at least 71%, about or at least 72%, about or at least 73%, about or at least 74%, about or at least 75%, about or at least 76%, about or at least 77%, about or at least 78%, about or at least 79%, about or at least 80%, about or at least 81%, about or at least 82%, about or at least 83%, about or at least 84%, about or at least 85%, about or at least 86%, about or at least 87%, about or at least 88%, about or at least 89%, about or at least 90%, about or at least 91%, about or at least 92%, about or at least 93%, about or at least 94%, about or at least 95%, about or at least 96%, about or at least 97%, about or at least 98%, about or at least 99% o about or at least r 100% yield.

The methods may form 2-(carboxymethyl)-4-nitrobenzoic acid (compound 1) with a purity of greater than or equal to about 60%, greater than or equal to about 65%, greater than or equal to about 70%, greater than or equal to about 75%, greater than or equal to about 80%, greater than or equal to about 85%, greater than or equal to about 90%, greater than or equal to about 95%, greater than or equal to about 96%, greater than or equal to about 97%, greater than or equal to about 98%, or greater than or equal to about 99%, as determined by HPLC.

The methods may further comprise reacting a compound of formula (I),

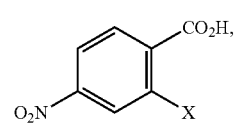

wherein X is halogen or $OSO_2R^a$; and $R^a$ is aryl, alkyl or haloalkyl; with a compound of formula

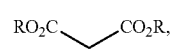

wherein R is alkyl; to form the compound of formula (III).

In certain embodiments, X is halogen. In certain embodiments, X is Cl. In certain embodiments, X is $SO_2R^a$; and $R^a$ is $C_1$-$C_6$ alkyl, aryl, or $C_1$-$C_6$ haloalkyl. In certain embodiments, X is $SO_2R^a$; and $R^a$ is methyl, 4-methylphenyl, or trifluoromethyl. In certain embodiments, the compound of formula (I) is 2-chloro-4-nitrobenzoic acid.

In certain embodiments, R is $C_1$-$C_6$ alkyl. In certain embodiments, R is $C_1$-$C_4$ alkyl. In certain embodiments, R is ethyl. In certain embodiments, the compound of formula (II) is diethyl malonate.

In certain embodiments, reacting a compound of formula (I) with a compound of formula (II) comprises adding a base. In certain embodiments, the base is a metal alkoxide. An alkoxide is the conjugate base of an alcohol. The metal alkoxide may be a lithium alkoxide, a sodium alkoxide, a potassium alkoxide, or a combination thereof. The metal alkoxide may comprise a $C_1$-$C_6$ alkyl group, as defined herein. In certain embodiments, the metal alkoxide is sodium methoxide.

In certain embodiments, reacting a compound of formula (I) with a compound of formula (II) comprises adding a catalyst. In certain embodiments, the catalyst comprises a transition metal. In certain embodiments, the transition metal is selected from the group consisting of palladium, platinum, nickel, rhodium, ruthenium, iridium, cobalt, iron, copper, gold silver, and combinations thereof. In certain embodiments, the transition metal is copper. In certain embodiments, the catalyst is copper (I) bromide. The catalyst loading in the reaction may be about 1 mol % to about 50 mol %, about 1 mol % to about 30 mol %, about 10 mol % to about 30 mol %, or about 15 mol % to about 25 mol %. The catalyst loading may be about or at least 1 mol %, about or at least 2 mol %, about or at least 3 mol %, about or at least 4 mol %, about or at least 5 mol %, about or at least 6 mol %, about or at least 7 mol %, about or at least 8 mol %, about or at least 9 mol %, about or at least 10 mol %, about or at least 11 mol %, about or at least 12 mol %, about or at least 13 mol %, about or at least 14 mol %, about or at least 15 mol %, about or at least 16 mol %, about or at least 17 mol %, about or at least 18 mol %, about or at least 19 mol %, about or at least 20 mol %, about or at least 21 mol %, about or at least 22 mol %, about or at least 23 mol %, about or at least 24 mol %, about or at least 25 mol %, about or at least 26 mol %, about or at least 27 mol %, about or at least 28 mol %, about or at least 29 mol %, about or at least 30 mol %, about or at least 35 mol %, about or at least 40 mol %, about or at least 45 mol %, or about or at least 50 mol %. The catalyst may be added in portions during the course of the conversion. The catalyst may be added such that the entirety of the catalyst is added at one time.

In certain embodiments, the reacting of a compound of formula (I) with a compound of formula (II) may further comprise adding a solvent or mixture of solvents. Any suitable solvent that is compatible with the components of the reaction mixture may be used. Suitably, a solvent will be selected such that the starting materials will be at least partially soluble (or fully soluble) and will allow the reaction mixture to be heated, if necessary, to a temperature sufficient for the reaction to produce the compound of formula (III). The solvents may include, but are not limited to: ethers such as diethyl ether, dibutyl ether, 1,2-dimethoxyethane, diglyme, t-butyl methyl ether, tetrahydrofuran and dioxane; aliphatic or aromatic hydrocarbon solvents such as benzene, xylene, toluene, hexane, and pentane; polar aprotic solvents such as acetonitrile, dimethylformamide, and dimethylsulfoxide; polar protic solvents such as methanol, ethanol, n-propanol, isopropanol, n-butanol, acetic acid and water; or any combination of two or more solvents. In certain embodiments, the solvent is ethanol.

In certain embodiments, the reacting of a compound of formula (I) with a compound of formula (II) may further comprise heating. For example, the reaction mixture may be heated at a temperature greater than ambient or room temperature, wherein ambient or room temperature is about 18° C. to about 25° C. The reaction mixture may be heated at a temperature of about 25° C. to about 90° C., or about 30° C. to about 80° C. The reaction mixture may be heated at a temperature of at least 25° C., at least 30° C., at least 35° C., at least 40° C., at least 45° C., at least 50° C., at least 55° C., at least 60° C., at least 65° C., at least 70° C., at least 75° C., at least 78° C., or at least 80° C. The reaction mixture may be heated at a temperature less than 90° C., less than 80° C., less than 78° C., less than 75° C., less than 70° C., less than 60° C., less than 55° C., less than 50° C., less than 45° C., less than 40° C., less than 35° C., or less than 30° C. The reaction mixture may be heated at a temperature of about 25° C., about 30° C., about 35° C., about 40° C., about 45° C., about 50° C., about 55° C., about 60° C., about 70° C., about 75° C., about 78° C., about 80° C., or about 90° C.

The methods may comprise allowing the conversion to proceed for a period of time sufficient to form the compound of formula (III). For example, the reaction may be allowed to proceed for about 1 hour to about 24 hours, about 2 hours to about 18 hours, or about 12 hours to about 18 hours.

The methods may form the compound of formula (III) in a yield of about 20% to 100%, e.g., about 20% to about 99%. The methods may provide the compound of formula (III) in about or at least 20%, about or at least 25%, about or at least 30%, about or at least 35%, about or at least 40%, about or at least 45%, about or at least 50%, about or at least 51%, about or at least 52%, about or at least 53%, about or at least 54%, about or at least 55%, about or at least 56%, about or at least 57%, about or at least 58%, about or at least 59%, about or at least 60%, about or at least 61%, about or at least 62%, about or at least 63%, about or at least 64%, about or at least 65%, about or at least 66%, about or at least 67%, about or at least 68%, about or at least 69%, about or at least 70%, about or at least 71%, about or at least 72%, about or at least 73%, about or at least 74%, about or at least 75%, about or at least 76%, about or at least 77%, about or at least 78%, about or at least 79%, about or at least 80%, about or at least 81%, about or at least 82%, about or at least 83%, about or at least 84%, about or at least 85%, about or at least 86%, about or at least 87%, about or at least 88%, about or at least 89%, about or at least 90%, about or at least 91%, about or at least 92%, about or at least 93%, about or at least 94%, about or at least 95%, about or at least 96%, about or at least 97%, about or at least 98%, about or at least 99% or about or at least 100% yield.

The methods may form the compound of formula (III) with a purity of greater than or equal to about 60%, greater than or equal to about 65%, greater than or equal to about 70%, greater than or equal to about 75%, greater than or equal to about 80%, greater than or equal to about 85%, greater than or equal to about 90%, greater than or equal to about 95%, greater than or equal to about 96%, greater than or equal to about 97%, greater than or equal to about 98%, or greater than or equal to about 99%, or greater than or equal to about 99.5% or greater than or equal to about 99.9% as determined by HPLC.

In an embodiment, the methods include reacting 2-chloro-4-nitrobenzoic acid (I-a) with diethylmalonate (II-a) to form 2-(1,3-diethoxy-1,3-dioxopropan-2-yl)-4-nitrobenzoic acid (III-a); reacting 2-(1,3-diethoxy-1,3-dioxopropan-2-yl)-4-nitrobenzoic acid (III-a) with a base to form 2-(carboxymethyl)-4-nitrobenzoic acid (compound 1); reacting 2-(carboxymethyl)-4-nitrobenzoic acid (compound 1) with urea to form 6-nitroisoquinoline-1,3(2H,4H)-dione (compound 2); reacting 6-nitroisoquinoline-1,3(2H, 4H)-dione (compound 2) with $R^1$—P(O)$Cl_2$ to form 1,3-dichloro-6-nitroisoquinoline (compound 3); and converting 1,3-dichloro-6-nitroisoquinoline (compound 3) to 6-aminoisoquinoline (compound 4) (Scheme 2).

Scheme 2

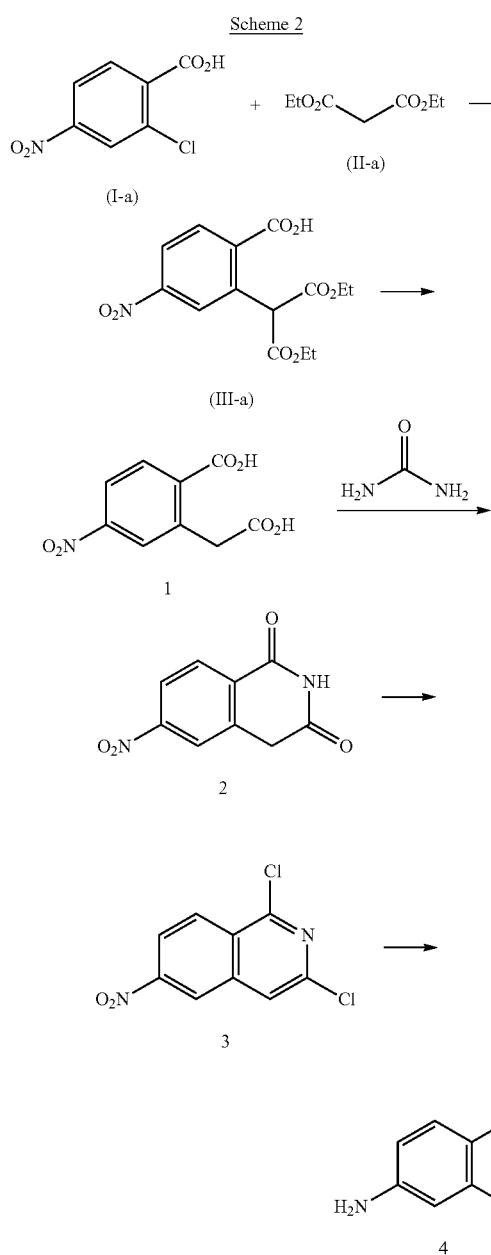

Scheme 3

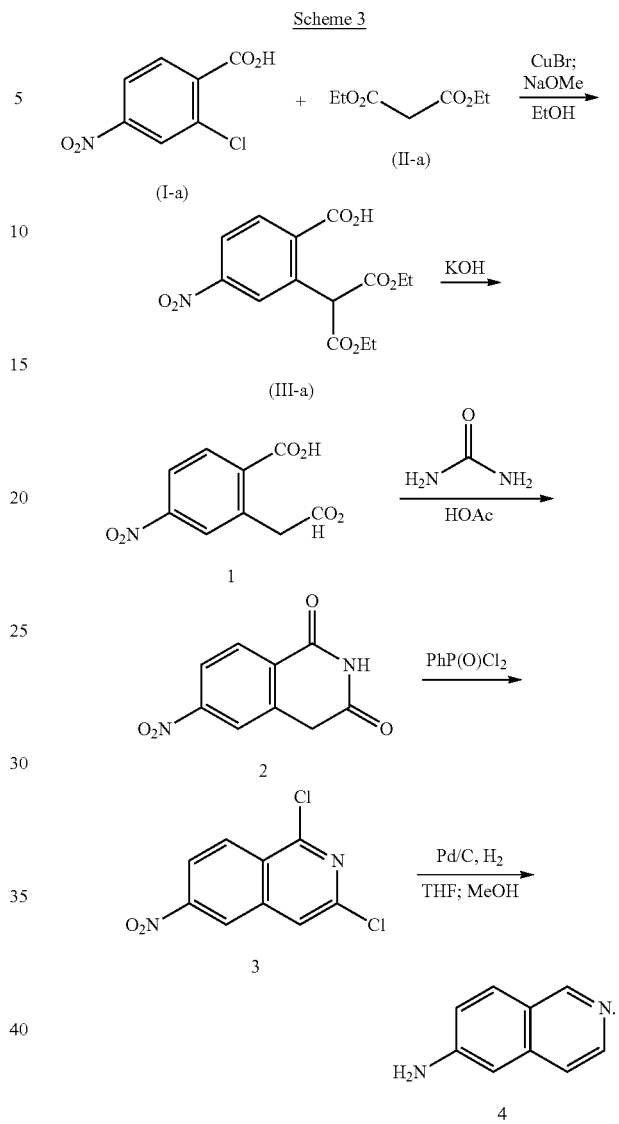

In a specific embodiment, the methods include reacting 2-chloro-4-nitrobenzoic acid (I-a) with diethylmalonate (II-a) in the presence of sodium methoxide and copper (I) bromide to form 2-(1,3-diethoxy-1,3-dioxopropan-2-yl)-4-nitrobenzoic acid (III-a); reacting 2-(1,3-diethoxy-1,3-dioxopropan-2-yl)-4-nitrobenzoic acid (III-a) with potassium hydroxide to form 2-(carboxymethyl)-4-nitrobenzoic acid (compound 1); reacting 2-(carboxymethyl)-4-nitrobenzoic acid (compound 1) with urea in acetic acid to form 6-nitroisoquinoline-1,3(2H,4H)-dione (compound 2); reacting 6-nitroisoquinoline-1,3(2H, 4H)-dione (compound 2) with phenylphosphonic dichloride to form 1,3-dichloro-6-nitroisoquinoline (compound 3); and converting 1,3-dichloro-6-nitroisoquinoline (compound 3) to 6-aminoisoquinoline (compound 4) by hydrogenation in the presence of palladium on carbon (Scheme 3).

Abbreviations which have been used in the descriptions of the above structures and schemes include: Ph for phenyl; Me for methyl; Et for ethyl; HOAc for acetic acid; and THF for tetrahydrofuran.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

In an embodiment, 6-aminoisoquinoline may be purified via a multi-step process. In embodiments, the multi-step process comprises (1) removal of insoluble impurities via filtration; (2) acid and base extraction; and (3) recrystallization.

Suitably, crude 6-aminoisoquinoline may be mixed with activated charcoal for a suitable time period in a solvent or a mixture of solvents to form a first mixture. The period of time may be at least about 4 hours. Any suitable solvent that is compatible with the components may be used. In an embodiment, the solvent may be methanol or ethanol.

The first mixture may be filtered through at least one filter to form a filtrate. The resulting filtrate may then be condensed and dissolved in an acidic solution to form a second mixture. The acidic solution may be, for example, a citric acid solution such as about or at least 5% citric acid. The second mixture is optionally heated to 35±5° C. for a period of time of 1-6 h. The resulting solution is washed at least one time with a solvent to form a third mixture. Any suitable solvent that is compatible with the components may be used. In an embodiment, the solvent may be dichloromethane. The resulting aqueous layer is mixed with a basic solution to form a precipitate. The basic solution may be, for example, concentrated ammonium hydroxide, 10% aqueous potassium hydroxide, 10% aqueous potassium carbonate, or combinations thereof. The resulting precipitate may be filtered and dried to obtain a solid.

The solid may be suspended in a solvent to form a suspension. Any suitable solvent that is compatible with the components may be used. In an embodiment, the solvent may be ethanol. The suspension may be heated to a temperature of about 75° C. for a period of time. The period of time may be about 45 minutes. Subsequently, the suspension is gradually cooled over the course of about 16 hours, and filtered to obtain 6-aminoisoquinonline. The methods may form 6-aminoisoquinonline with a purity of greater than or equal to 99%, as determined by HPLC. The steps recited in this paragraph may be repeated as necessary, e.g., one time, two times, three times, etc.

The filters may be nylon or PTFE filters.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, combinations thereof and the like.

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Routine experimentation, including appropriate manipulation of the reaction conditions, reagents and sequence of the synthetic route, protection of any chemical functionality that is not compatible with the reaction conditions, and deprotection at a suitable point in the reaction sequence of the methods are included in the scope of the invention. Suitable protecting groups and the methods for protecting and deprotecting different substituents using such suitable protecting groups are well known to those skilled in the art; examples of which can be found in PGM Wuts and TW Greene's book entitled Protective Groups in Organic Synthesis (4$^{th}$ ed.), John Wiley & Sons, NY (2006), which is incorporated herein by reference in its entirety. It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

It should be understood that a compound may possess tautomeric forms, as well as geometric isomers, and that these forms also constitute an aspect of the invention.

The present disclosure also includes isotopically-labeled compounds, which are identical to any of those recited in the methods, but for the fact that one or more positions in the molecule are enriched with an isotope of the same atom, having an atomic mass or mass number that is different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^5$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example, increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described herein. Examples using appropriate isotopically-labeled reagent in place of non-isotopically-labeled reagent.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

The compounds and processes of the invention will be better understood by reference to the following examples, which are intended as an illustration of and not a limitation upon the scope of the invention.

3. Examples

Unless otherwise stated, temperatures are given in degrees Celsius (° C.); synthetic operations were carried out at ambient temperature, "rt," or "RT," (typically a range of from about 18-25° C.); evaporation of solvents was carried out using a rotary evaporator under reduced pressure (typically, 4.5-30 mm Hg) with a bath temperature of up to 60° C.; the course of reactions was typically followed using thin layer chromatography (TLC); all melting points, if given, are uncorrected; all intermediates as well as the final product exhibited satisfactory 1H-NMR, HPLC and/or microanalytical data; and the following conventional abbreviations are used: L (liter(s)), mL (milliliters), mmol (millimoles), g (grams), mg (milligrams), min (minutes), and h (hours).

Proton magnetic resonance ($^1$H NMR) spectra were recorded on a Varian Mercury 300 MHz ($^1$H) NMR spectrometer. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz).

Abbreviations in the following experimentals include: DMSO—dimethylsulfoxide; EtOAc—ethyl acetate; EtOH—ethanol; HOAc—acetic acid; MeOH—methanol; MTBE—methyl tert-butyl ether; Pd/C—palladium on carbon; THF—tetrahydrofuran; and TLC—thin layer chromatography.

Example 1: 2-(Carboxymethyl)-4-nitrobenzoic acid (1)

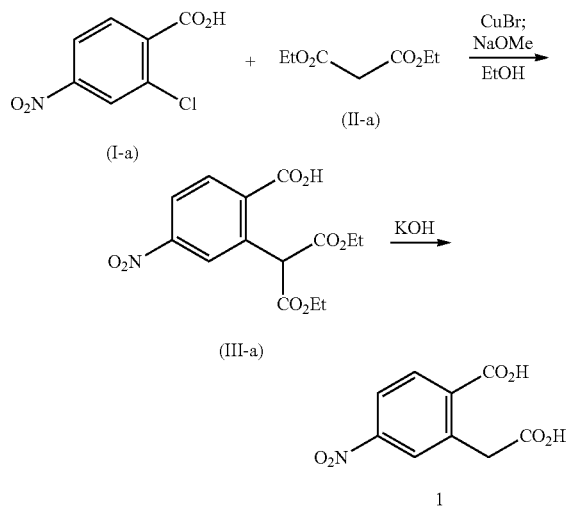

2-(1,3-Diethoxy-1,3-dioxopropan-2-yl)-4-nitrobenzoic acid (III-a):

Under an atmosphere of nitrogen, a mixture of diethyl malonate (18 L, 118.1 mol) and 2-chloro-4-nitrobenzoic acid (9 kg, 44.6 mol) was added to a solution of NaOMe (7.2 kg, 133.3 mol, 3 eq) in EtOH (45 L), followed by the addition of CuBr (1.26 kg). The resulting mixture was stirred under reflux overnight (~16 h). After the essentially complete consumption of 2-chloro-4-nitrobenzoic acid was indicated by TLC, the reaction was cooled and concentrated. The residue was diluted with water (~100 L) and washed with MTBE (25 L×2). The organic layer was discarded to provide the title compound as an aqueous solution. The crude product was carried on without further purification.

2-(Carboxymethyl)-4-nitrobenzoic acid (1):

The aqueous layer of the crude 2-(1,3-diethoxy-1,3-dioxopropan-2-yl)-4-nitrobenzoic acid was charged into a 100 L reactor, followed by the addition of solid KOH (7.58 kg, 135.3 mol). The basic reaction mixture was stirred at RT overnight. After 2-(1,3-diethoxy-1,3-dioxopropan-2-yl)-4-nitrobenzoic acid was consumed as indicated by HPLC analysis, the reaction mixture was carefully acidified with concentrated HCl to pH 6~7. EtOAc (50 L) was then added and the mixture was further acidified with concentrated HCl to pH 2~3. The organic layer was separated. The aqueous layer was extracted with EtOAc (40 L×2). The combined organic layers were washed with water (10 L×2) and brine (10 L), dried over anhydrous Na$_2$SO$_4$, filtered and concentrated to remove about half the solvent. The resulting solid was filtered and washed with EtOAc to provide the title compound as a yellow solid (5 kg, yield 49.7%). HPLC purity: 98.2%; $^1$H-NMR (300 MHz, DMSO-d$_6$) δ 13.0 (s, 2H), 8.28 (d, J=2.2 Hz, 1H), 8.21 (dd, J=8.6 Hz, 2.3, 1H), 8.09 (d, J=8.6 Hz, 1H), 4.10 (s, 2H).

Example 2: 6-Nitroisoquinoline-1,3(2H,4H)-dione (2)

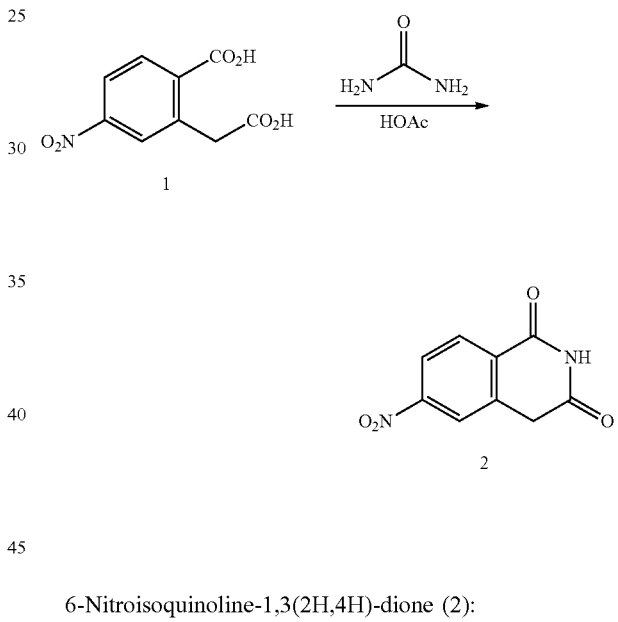

6-Nitroisoquinoline-1,3(2H,4H)-dione (2):

A suspension of 2-(carboxymethyl)-4-nitrobenzoic acid (1.5 kg, 6.67 mol, 1 eq) in acetic acid (6 L) was heated at 110° C. The suspension became a clear solution when the temperature reached 90° C. Solid urea (2.85 kg, 47.5 mol, 7.1 eq) was then added slowly into the reaction mixture. The reaction was stirred at 110° C. for about 4 h. The reaction mixture was combined with another parallel batch (from 1.5 kg of 2-(carboxymethyl)-4-nitrobenzoic acid) and poured into a mixture of ice water (20 kg) and stirred for 0.5 h. The resulting solid was filtered and washed with water (10 L×3) and air dried to produce the title compound as a tan solid (2 kg, yield 72.8%). $^1$H-NMR (300 MHz, DMSO-d$_6$) δ 11.61 (s, 2H), 8.30 (s, 1H), 8.24 (s, 1H), 4.17 (s, 2H).

Three batches of the title compound were produced using the procedure above. Two batches employing 1.5 kg of 2-(carboxymethyl)-4-nitrobenzoic acid provided 2 kg total of the title compound (73% yield); one batch employing 1.8 kg of 2-(carboxymethyl)-4-nitrobenzoic acid provided 1.38 kg of the title compound (84% yield).

Example 3: 1,3-Dichloro-6-nitroisoquinoline (3)

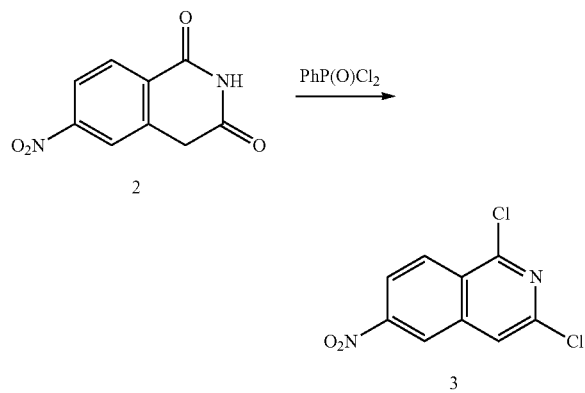

1,3-Dichloro-6-nitroisoquinoline (3):

A solution of 6-nitroisoquinoline-1,3(2H,4H)-dione (1.8 kg, 8.74 mol, 1 eq) in phenylphosphonic dichloride (3.73 L) was heated at 140° C. and stirred for 3 h. After complete consumption of the starting material was indicated by TLC, the reaction mixture was cooled to 100° C. and then poured into a mixture of EtOAc (45 L) and ice water (5 kg). The mixture was stirred at RT for 0.5 h. The solid was filtered off. The filtrate was washed with aqueous $NaHCO_3$ until the pH value of the organic layer became 7, and followed by a brine wash. The organic layer was dried over anhydrous $Na_2SO_4$ and passed through a pad of silica gel. The filtrate was concentrated and the resulting solid product was collected by filtration to produce the title compound as a yellow solid (1.41 kg, 66.2% yield). HPLC purity: 98.7%; $^1$H-NMR (300 MHz, $CDCl_3$) δ 8.73 (d, J=2.1 Hz, 1H), 8.53 (d, J=9.2 Hz, 1H), 8.44 (dd, J=9.8 Hz, 2.1 Hz, 1H), 7.90 (s, 1H).

Two batches of the title compound were produced using the procedure above. One batch employing 1.8 kg of 6-nitroisoquinoline-1,3(2H,4H)-dione provided 1.41 kg of the title compound (66% yield); one batch employing 1.08 kg of 6-nitroisoquinoline-1,3(2H, 4H)-dione provided 0.8 kg of the title compound (63% yield).

Example 4: 6-Aminoisoquinoline (4)

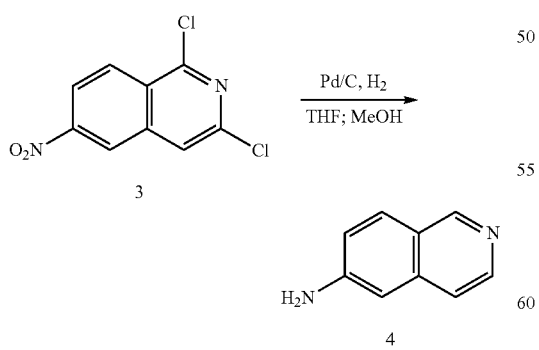

6-Aminoisoquinoline (4):

1,3-Dichloro-6-nitroisoquinoline (700 g, 2.88 mol, 1 eq) and 10% Pd/C (45 g, 6.5% w/w) were suspended in THF (5.5 L). After purging with a nitrogen/hydrogen cycle three times, the reaction mixture was hydrogenated at 45° C. under a pressure of 0.6 MP for about 6~8 h until the nitro group was fully reduced to the amino group. Partial formation of the des-chloride intermediate was also indicated by TLC and HPLC analysis. After the pressure of the reactor was released, $K_2CO_3$ (1 kg), MeOH (1.5 L), and additional Pd/C (10%, 45 g) were added to the reaction suspension. After purging with a nitrogen/hydrogen cycle three times, the reaction mixture was hydrogenated at 45° C. under a pressure of 0.6 MP until completion of the reaction (2-3 days). The reaction mixture was filtered through a pad of Celite and washed with MeOH (500 mL×2). The filtrate was concentrated under reduced pressure. The resulting residue (~550 g, wet) was slurried in MeOH (550 mL, 1 vol) for ~0.5 h and filtered to produce the title compound as a green solid (380 g). The crude 6-aminoisoquinoline was combined with another two parallel batches of crude 6-aminoisoquinoline and purified together. The combined crude 6-aminoisoquinoline batches (green solid) were de-colored by active charcoal (~10%) in THF/MeOH to produce 6-aminoisoquinoline as a gray solid (1.05 kg, yield 85.6%). HPLC purity: 99.1%; LCMS (ESI+): m/z 145 (M+H); $^1$H-NMR (300 MHz, DMSO-$d_6$) δ 8.84 (s, 1H), 8.14 (d, J=6.0 Hz, 1H), 7.73 (d, J=9.0 Hz, 1H); 7.33 (d, J=6 Hz, 1H); 7.03-6.99 (m, 1H); 6.70 (s, 1H); 5.96 (s, 2H).

Example 5. Purification Process

To a 50 L reactor was charged 1000 g of 6-aminisioquinoline and 25 L of methanol. The mixture was treated with 100 g of activated charcoal and stirred for NLT 4 h. The charcoal was filtered on a Nylon or PTFE filter. The filtrates were concentrated in vacuo and the residue partially dissolved in 15 L of 5% aqueous citric acid. The resulting pH 5 aqueous mixture was warmed to 35° C. and washed with three 7.5-L portions of dichloromethane. The pH of the upper aqueous layer was adjusted to 11 with 3 L of 30% ammonium hydroxide and the solid that precipitated was filtered. After drying to constant weight, the solid iwas recrystallized from 10.8 L of hot ethanol to afford 646 g (64.6% recovery) of a solid whose structure was confirmed to be 6-aminoisoquinoline by $^1$H NMR. Purity by HPLC: 100%.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of preparing 6-aminoisoquinoline,

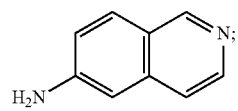

the method comprising:
reacting 6-nitroisoquinoline-1,3(2H,4H)-dione,

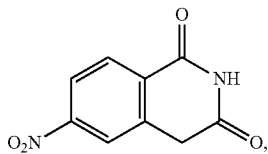

with R¹—P(O)Cl₂, wherein R¹ is aryl, alkyl, or chloro;
to form 1,3-dichloro-6-nitroisoquinoline,

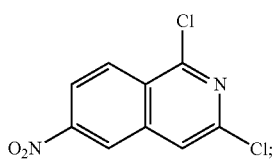

converting 1,3-dichloro-6-nitroisoquinoline to crude 6-aminoisoquinoline;
decolorizing the 6-aminoisoquinoline;
dissolving the 6-aminoisoquinoline in an acidic solution and washing with solvent;
extracting with base; and
recrystallizing to obtain about 99.9% pure 6-aminoisoquinoline;
wherein reacting 6-nitroisoquinoline-1,3(2H,4H)-dione with R¹—P(O)Cl₂ comprises heating at a temperature of at least 120° C.

2. The method of claim 1, wherein R¹ is aryl.

3. The method of claim 1, further comprising:
reacting 2-(carboxymethyl)-4-nitrobenzoic acid,

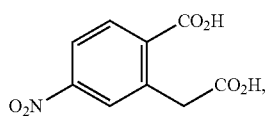

with urea in the presence of an acid;
to form 6-nitroisoquinoline-1,3(2H,4H)-dione.

4. The method of claim 3, wherein reacting 2-(carboxymethyl)-4-nitrobenzoic acid with urea comprises heating at a temperature of at least 90° C.

5. The method of claim 3, wherein the acid is acetic acid.

6. The method of claim 3, further comprising:
reacting a compound of formula (III),

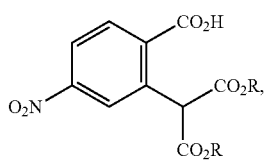

wherein R is alkyl;
with a base, to form 2-(carboxymethyl)-4-nitrobenzoic acid.

7. The method of claim 6, wherein the base is an alkali metal hydroxide or an alkaline earth metal hydroxide.

8. The method of claim 6, wherein the base is an alkali metal hydroxide.

9. The method of claim 6, wherein the base is potassium hydroxide.

10. The method of claim 6, further comprising:
reacting a compound of formula (I),

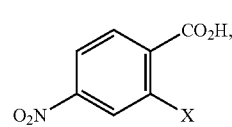

wherein X is halogen or OSO₂Rᵃ; and Rᵃ is aryl, alkyl or haloalkyl;
with a compound of formula (II),

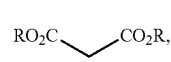

wherein R is alkyl;
to form the compound of formula (III).

11. The method of claim 10, wherein reacting the compound of formula (I) with the compound of formula (II) comprises adding a base, a catalyst, and a solvent.

12. The method of claim 11, wherein the base is a metal alkoxide.

13. The method of claim 11, wherein the catalyst comprises copper.

14. The method of claim 11, wherein the solvent is ethanol.

15. The method of claim 10, further comprising heating at a temperature of at least 60° C.

16. The method of claim 6, wherein R is C₁-C₆ alkyl.

17. The method of claim 6, wherein R is ethyl.

18. The method of claim 10, wherein X is halogen.

19. The method of claim 10, wherein X is Cl.

20. The method of claim 1, wherein the 6-aminoisoquinoline is decolorized with activated charcoal.

21. The method of claim 1, wherein the crude 6-aminoisoquinioline is filtered using methanol.

22. The method of claim 1, wherein the acid is citric acid.

23. The method of claim 1, wherein the base is concentrated ammonium hydroxide, 10% aqueous potassium hydroxide, and 10% aqueous potassium carbonate.

24. The method of claim 1, wherein the 6-aminoisoquinioline is recrystallized using ethanol.

25. The method of claim 1, wherein the 6-aminoisoquinoline is at least about 99.9% pure.

26. The method of claim 25, wherein the 6-aminoisoquinoline is substantially free of higher molecular weight impurities, nitroso and nitro containing impurities, and chlorinated impurities.

27. A method of preparing 6-aminoisoquinoline,

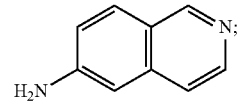 [SMILES: Nc1ccc2cnccc2c1]

the method comprising:
(a) reacting 2-chloro-4-nitrobenzoic acid,

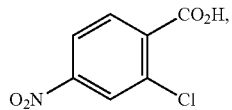

with diethyl malonate, to form 2-(1,3-diethoxy-1,3-dioxopropan-2-yl)-4-nitrobenzoic acid,

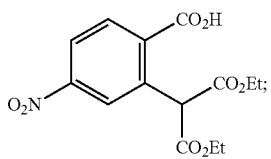 [SMILES: CCOC(=O)C(C(=O)OCC)c1cc([N+](=O)[O-])ccc1C(=O)O]

(b) reacting 2-(1,3-diethoxy-1,3-dioxopropan-2-yl)-4-nitrobenzoic acid with a base to form 2-(carboxymethyl)-4-nitrobenzoic acid,

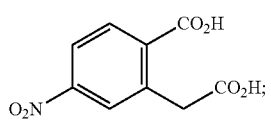 [SMILES: O=C(O)Cc1cc([N+](=O)[O-])ccc1C(=O)O]

(c) reacting 2-(carboxymethyl)-4-nitrobenzoic acid with urea to form 6-nitroisoquinoline-1,3(2H,4H)-dione,

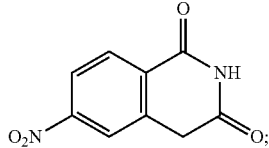 [SMILES: O=C1Cc2cc([N+](=O)[O-])ccc2C(=O)N1]

(d) reacting 6-nitroisoquinoline-1,3(2H,4H)-dione with $R^1$—P(O)Cl$_2$ to form 1,3-dichloro-6-nitroisoquinoline,

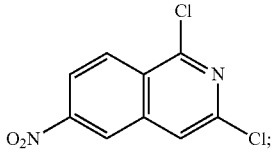

wherein $R^1$ is aryl;
(e) converting 1,3-dichloro-6-nitroisoquinoline to 6-aminoisoquinoline;
(f) decolorizing the 6-aminoisoquinoline;
(g) dissolving the 6-aminoisoquinoline in an acidic solution and washing with solvent;
(h) extracting with base; and
(i) recrystallizing to obtain 99.9% pure 6-aminoisoquinoline.

* * * * *